United States Patent [19]

Jaffe

[11] 4,342,709

[45] Aug. 3, 1982

[54] PROCESS FOR PRODUCING DIETHYL PHOSPHITE

[75] Inventor: Fred Jaffe, Ossining, N.Y.

[73] Assignee: Stauffer Chemical Company, Westport, Conn.

[21] Appl. No.: 214,072

[22] Filed: Dec. 8, 1980

[51] Int. Cl.$^3$ .............................................. C07F 9/141
[52] U.S. Cl. .................................... 260/978; 260/967
[58] Field of Search .............................. 260/967, 978

[56] References Cited

U.S. PATENT DOCUMENTS 2,834,797  5/1958  Chadwick ........................... 260/967
3,019,249  1/1962  Gunderloy, Jr. .................... 260/967

*Primary Examiner*—Anton H. Sutto
*Attorney, Agent, or Firm*—Vivienne T. White

[57] ABSTRACT

A process of producing diethyl phosphite by reacting an excess of triethyl phosphite with phosphorous acid. The improved process results in a high quality diethyl phosphite product having low acidity that is suitable as an intermediate for most uses requiring a low acidity diethyl phosphite.

6 Claims, No Drawings

PROCESS FOR PRODUCING DIETHYL PHOSPHITE

BACKGROUND OF THE INVENTION

1. Field of the Invention

The invention relates to the production of diethyl phosphite of high purity and low acidity.

2. Relevant Prior Art

Diethyl phosphite is useful as an intermediate in the production of organophosphorous compounds such as flame retardant compounds and as stabilizers for plastics.

U.S. Pat. No. 2,834,797 discloses a method of producing dialkyl phosphites by the reaction of trialkyl phosphites with molten phosphorous acid. The cited patent teaches reacting a trialkyl phosphite with phosphorous acid in a molar ratio of phosphite to phosphorous acid of about 1:2 to 3:1 and preferably 2:1 for maximum dialkyl phosphite yields. The diethyl phosphite prepared as disclosed in the cited patent is said to result in a 78% of theory yield after distillation, based on triethyl phosphite. Additionally, the dialkyl phosphite product produced in accordance with the process of the cited art has been found to have an acid value in excess of 20.2 milligrams KOH per gram, which for certain applications utilizing diethyl phosphite (for instance, in producing aminoalkyl phosphonates used as fire retardants in urethane foams) would reduce the product yield and additionally would decrease the product purity and prevent it from meeting acidity specification. In such applications an acid value of less than 10 mg of KOH per gm of product is desirable. However, an acid value of less than 5 mg of KOH per gram is preferred.

An object of the invention is to produce a diethyl phosphite product of high purity, having low acidity in high yields without requiring further distillation.

SUMMARY OF THE INVENTION

It was unexpectedly discovered that the use of a 0.05–0.30 molar excess of triethyl phosphite over stoichiometric quantities in producing diethyl phosphite by the reaction of triethyl phosphite with phosphorous acid, significantly increases the product purity and product yield while significantly decreasing the acidity of the diethyl phosphite product.

The invention is a process for producing diethyl phosphite of increased purity and low acidity comprising reacting from about 2.05–2.30 or desirably about 2.08 to about 2.20 moles of triethyl phosphite, per mole of phosphorous acid. The novel process disclosed herein provides a diethyl phosphite product in a yield of about 100% based on phosphorous acid, with purity in excess of 95%, which obviates the need for further purification by distillation; and acidities in the range of 1.5 to 3.5 milligrams of KOH per gram of product. Residual triethyl phosphite reactant was found to be in the range of 0.1 to 2.0%.

DETAILED DESCRIPTION OF THE INVENTION

The invention provides a process wherein triethyl phosphite is added to anhydrous phosphorous acid, in an amount over stoichiometric quantities, and heated for a period of time to give a low acid, high purity and high yield diethyl phosphite product without the need for further purification treatment as by distillation. The product produced in this manner is particularly desirable for preparing quality aminoalkyl phosphonates utilized as flame retardant compounds in urethane foam products.

The following reaction is believed to exemplify the process of producing diethyl phosphite by reaction of triethyl phosphite and phosphorous acid:

$$2P(OC_2H_5)_3 + HPO_3H_2 \rightarrow 3HPO_3(C_2H_5)_2$$

To achieve the low acid, high yield and high purity diethyl phosphite product disclosed herein, about a 2.5–15.0 mole percent excess of triethyl phosphite, or more desirably, about a 4–10 mole percent excess, is used in accordance with the invention. Preferably, about a 7.5 mole percent excess triethyl phosphite is reacted with the phosphorous acid in accordance with the invention.

As oxygen can cause oxidation of the phosphorous acid to phosphoric acid, and oxidation of the triethyl phosphite to triethyl phosphate, precaution should include avoidance of oxygen during the process.

In addition, since phosphorous acid is hygroscopic and deliquescent, the reactor should be purged with an inert gas, preferably nitrogen, prior to charging the reactants to the reactor. The phosphorous acid is generally added to the reactor over a period of time and under an inert gas purge to avoid absorption of water from the atmosphere.

Any gases exiting the reactor generally contain low levels of phosphine, which may be scrubbed from the exiting gas by known methods as, for instance, scrubbing with dilute sodium hypochlorite to remove the dangerous contaminant.

The anhydrous phosphorous acid can be charged to the reactor with or without prior heating of the reactor. Generally, however, the reactor which may contain a product heel is heated to 40° C. The mixture, after addition of the phosphorous acid is then heated to 80° C. and triethyl phosphite is gradually added.

The reaction process is the same with or without utilizing a product heel. It is, therefore, not necessary to utilize a product heel in the act of practicing this invention. If a product heel is utilized, the phosphorous acid and the heel may be mixed with or without the application of heat to the reactor prior to dissolving the phosphorous acid. It is desirable, however, to heat the mixture to a temperature of from about 40°–80° C. prior to adding triethyl phosphite.

In the practice of the invention, the process is conducted at a temperature of from about 60°–150° C., generally at 80°–120° C. and preferably from 90°–110° C.

At temperatures below 75° C., the reaction is sluggish. Higher temperatures are preferred to avoid increasing the unreacted triethyl phosphite content and to increase the reaction rate. Using the amount of triethyl phosphite over stoichiometric quantities, as disclosed herein causes complete reaction and advantageously provides a low acid product. Temperatures about 130° C. should be avoided since they can result in some increase decomposition of the acid to phosphoric acid and phosphine. Although some trace amount of phosphine is found under the reaction conditions disclosed herein, this small amount can be scrubbed from the exit gas as noted above.

Use of increased amounts of triethyl phosphite over that disclosed herein for reacting with phosphorous acid would not only decrease the acidity of the final product but also decrease the overall purity of the diethyl phosphite product since some amounts of unreacted triethyl phosphite would remain in the product. Similarly, use of stoichiometric quantities of the reactants or less than the amount disclosed herein would result in decreased purity, and increase the acidity of the product.

The reaction is exothermic and can be controlled somewhat by adjusting the addition rate of triethyl phosphite.

In the preferred process of practicing the invention, phosphorous acid can be added to the reactor at temperatures of from about 40°–80° C., particularly where a diethyl phosphite heel is present. The addition of triethyl phosphite can desirably occur at temperatures of from about 80°–130° C. During the triethyl phosphite phosphorous acid reaction period, temperatures of about 90°–110° C. are preferred. It should be obvious to one skilled in the art that, utilizing reaction temperatures at the lower end of the specified range will result in a slower reaction rate and require a longer time period to obtain a product having the desired acidity level.

The following Examples are illustrative of the invention. Yields of about 100% based on phosphorous acid were obtained in all process Examples provided below for the diethyl phosphite product.

EXAMPLE 1

Diethyl phosphite (DEP) was produced by reacting 357.0 grams (2.10 moles) of triethyl phosphite in a reactor purged with nitrogen, with 82 grams of phosphorous acid (1.0 moles). The triethyl phosphite (TEP) representing a 7.5% excess over stoichiometric quantities was added to the reactor containing the phosphorous acid and a diethyl phosphite heel of 82 grams at 80° C., over a 30 minute period. During the addition of triethyl phosphite, the temperature was maintained at from 85°–86° C. by the rate of addition. Thereafter, the temperature was raised to 95° C. and the reactants were heated over a period of 4 hours to produce a diethyl phosphite product having a 97.9% purity and an acid value of 3.34 mg KOH/gm.

EXAMPLE 2

The process of Example 1 was repeated except that the reactants were heated to a temperature of 110° C., instead of 95° C., after the triethyl phosphite addition. The purity of the diethyl phosphite obtained after 5 hours of heating was 97.1% with a KOH acid number of 2.24.

EXAMPLE 3

The process of Example 1 was followed using 348.6 grams of triethyl phosphite representing a 5% excess. The diethyl phosphite product had a purity of 97.9% after 5 hours of heating at 95° C. and the KOH acid number was 4.02.

COMPARATIVE EXAMPLE A

Diethyl phosphite was prepared by reacting triethyl phosphite with phosphorous acid in a molar ratio of 2:1. A solvent heel of 41 grams of diethyl phosphite having an acid value of 3.08 mg/KOH/gm. was utilized in the process. The diethyl phosphite heel was heated to 75° C. prior to adding the phosphorous acid. The triethyl phosphite was added at temperatures between 75°–85° C. over a 30 minute period and the temperature was then raised to 95° C. The acidity of the product obtained over a five hour reaction period is given below.

| Time at 95° C. (Hrs.) | Acidity mg/KOH/gm |
| --- | --- |
| 0.5 | 22.4 |
| 2.5 | 20.5 |
| 3.5 | 20.2 |
| 5.0 | 23.0 |

The acidity of the diethyl phosphite product obtained would have been higher if a solvent heel possessing high acidity had been used. In order to achieve acidity levels of <10 mg/KOH/gm., and a purity level in excess of 95%, the product of the above would have to be distilled which would result in some product loss and, therefore, lower the yield of diethyl phosphite.

COMPARATIVE EXAMPLE B

Triethyl phosphite was reacted with phosphorous acid in a 2:1 molar ratio in a reactor. The reactor was slowly heated to between 70°–95° C. during the reaction period shown below. The following results were obtained from samples removed over the reaction period.

| Heating Time (hrs.) | Temperature | Acidity (mg/KOH/gm) |
| --- | --- | --- |
| 1 | 70–75° | 23.23 |
| 1½ | 80–95° | 22.16 |
| 2½ | 80–95° | 22.16 |

EXAMPLE 4

Three batches of diethyl phosphite were prepared in a plant operation using amounts of reactants as specified below.

|  | Batch 1 | Batch 2 | Batch 3 |
| --- | --- | --- | --- |
| TEP (kgs) | 60.46 | 60.55 | 60.60 |
| DEP Heel (kgs) | 29.5 | 29.5 (from Batch 1) | 29.5 (from Batch 2) |
| Phosphorous Acid (kgs) | 13.9 | 13.9 | 13.9 |
| % excess TEP | 7.5 | 7.5 | 7.5 |

In the process the diethyl phosphite heel was charged to the reactor and heated to 40° C. Phosphorous acid was then added in the amount specified and the reactor maintained under a constant nitrogen purge. The reactor contents were then heated to 80° C. and the triethyl phosphite was added as the temperature was maintained at between 80°–110° C. Toward the end of the addition of the triethyl phosphite, the temperature was maintained between 100°–110° C. and held for a period of 5 hours. The following results were obtained:

|  | Batch 1 | Batch 2 | Batch 3 |
| --- | --- | --- | --- |
| Purity wt. % | 97.5 | 96.4 | 97.2 |
| Acidity mg/KOH/g | 2.2 | 2.4 | 2.1 |
| Specific Gravity | 1.072 | 1.071 | 1.070 |
| Refractive Index $N_D{}^{25}$ | 1.407 | 1.405 | 1.405 |
| Color, APHA | 40 | 40–50 | 25 |

What is claimed:

1. A process for producing diethyl phosphite of low acidity, high yields and increased purity comprising reacting triethyl phosphite with phosphorous acid in a reactor in a molar ratio of from about 2.05:1 to about 2.30:1.

2. The process of claim 1 wherein said molar ratio is from about 2.08:1 to about 2.20:1.

3. The process of claim 1 wherein said molar ratio is about 2.15:1.

4. The process of claim 1 or 2 or 3, wherein triethyl phosphite is reacted with phosphorous acid at a temperature of from about 60° to about 150° C.

5. The process of claim 4 wherein triethyl phosphite is reacted with phosphorous acid at a temperature of from about 80° to about 130° C.

6. The process of claim 5 wherein said temperature is from about 90° to about 110° C.

* * * * *